United States Patent
Parton et al.

(10) Patent No.: US 10,550,067 B2
(45) Date of Patent: *Feb. 4, 2020

(54) LEVULINIC ACID COMPOSITIONS

(71) Applicant: GFBIOCHEMICALS IP ASSETS B.V., Geleen (NL)

(72) Inventors: Rudy Francois Maria Jozef Parton, Geleen (NL); Aris De Rijke, Geleen (NL)

(73) Assignee: GFBIOCHEMICALS IP ASSETS B.V., Geleen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/743,093

(22) PCT Filed: Jul. 8, 2016

(86) PCT No.: PCT/EP2016/066242
§ 371 (c)(1),
(2) Date: Jan. 9, 2018

(87) PCT Pub. No.: WO2017/009217
PCT Pub. Date: Jan. 19, 2017

(65) Prior Publication Data
US 2019/0077740 A1    Mar. 14, 2019

(30) Foreign Application Priority Data

Jul. 10, 2015 (EP) .................................. 15176305

(51) Int. Cl.
| | | |
|---|---|---|
| *C07C 59/185* | (2006.01) | |
| *C07C 51/43* | (2006.01) | |
| *C07C 51/47* | (2006.01) | |
| *C07C 51/44* | (2006.01) | |
| *B01D 1/00* | (2006.01) | |
| *B01D 1/06* | (2006.01) | |
| *B01D 9/00* | (2006.01) | |
| *C07D 307/08* | (2006.01) | |

(52) U.S. Cl.
CPC .......... *C07C 59/185* (2013.01); *B01D 1/0094* (2013.01); *B01D 1/065* (2013.01); *B01D 9/0031* (2013.01); *C07C 51/43* (2013.01); *C07C 51/44* (2013.01); *C07C 51/47* (2013.01); *C07D 307/08* (2013.01)

(58) Field of Classification Search
CPC ....... C07C 59/185; C07C 51/43; C07C 51/44; C07C 51/47; B01D 1/0094; B01D 9/0031; B01D 1/065; C07D 307/08
See application file for complete search history.

(56) References Cited

U.S. PATENT DOCUMENTS

| | | | |
|---|---|---|---|
| 2,305,738 A | * | 12/1942 | Scheuing ................ C07C 51/00 562/515 |
| 4,236,021 A | | 11/1980 | Hsu et al. |
| 4,897,497 A | | 1/1990 | Fitzpatrick |
| 5,189,215 A | | 2/1993 | Farnleitner et al. |
| 5,608,105 A | | 3/1997 | Fitzpatrick |
| 6,054,611 A | | 4/2000 | Farone et al. |
| 2010/0312006 A1 | | 12/2010 | Lake et al. |

FOREIGN PATENT DOCUMENTS

| | | |
|---|---|---|
| WO | 2010030617 A1 | 3/2010 |
| WO | 2013034763 A1 | 3/2013 |
| WO | 2014037560 A1 | 3/2014 |
| WO | WO2014037560 * | 3/2014 |
| WO | 2014087013 A1 | 6/2014 |
| WO | 2014087015 A1 | 6/2014 |
| WO | 2014087017 A1 | 6/2014 |
| WO | 2014173995 A1 | 10/2014 |

OTHER PUBLICATIONS

B. Girisuta et al., Green Chemicals, Chemical Engineering Research and Design, May 2006, pp. 339-349, 84 (A5), Trans IChemE AG, Groningen, The Netherlands.
AIChE Annual Meeting, The Stability of Levulinic Acid During Acid-Catalyzed Glucose Dehydration, Nov. 3, 2013, pp. 1-2.
P. J. Jansens and M. Matsuoka, Melt Crystallization, Crystallization, 2000, pp. 966-975, Academic Press.
G.F. Arkenbout, Chapter 11, Technical Equipment for Crystal Layer Growth, Melt Crystallization Technology, 1995, pp. 239-293.

* cited by examiner

*Primary Examiner* — Jafar F Parsa
*Assistant Examiner* — Blaine G Doletski
(74) *Attorney, Agent, or Firm* — Hudak, Shunk & Farine Co. LPA

(57) ABSTRACT

A levulinic acid composition A having: a. at least 95 wt. % of levulinic acid; b. between 5 wppm and 5000 wppm of formic acid; and c. less than 1000 wppm of angelica lactone, based on the total weight of the composition. A process for the isolation of a levulinic acid composition, having the following steps: a. performing acid catalyzed hydrolysis of a C6 carbohydrate-containing feedstock to obtain reaction product X, b. subjecting of reaction product X to solid-liquid separation to provide a composition 1, c. feeding composition 1 to at least two purification steps to treat composition 1 to obtain a levulinic acid composition, wherein a second or a further purification step is a melt crystallization step.

17 Claims, No Drawings

LEVULINIC ACID COMPOSITIONS

FIELD OF THE INVENTION

The present invention is directed to a levulinic acid composition, to a process for the production of a levulinic acid composition and to the use of a levulinic acid composition.

BACKGROUND OF THE INVENTION

Levulinic acid, or 4-oxopentanoic acid, is an organic compound with the formula $CH_3C(O)CH_2CH_2CO_2H$. Levulinic acid as such is used as preservative in food and cosmetic applications. It can be derived from degradation of cellulose that is for example present in agricultural waste products, waste from the paper industry or municipal waste but also in lignocellulosic biomass such as wood and grass.

Levulinic acid is a precursor to pharmaceuticals, plasticizers, and various other additives.

Biofuels can also be prepared from levulinic acid including methyltetrahydrofuran (MeTHF), gamma-valerolactone, and ethyl levulinate.

In the prior art several processes for the production of levulinic acid are described.

Levulinic acid can, for example, be produced from diethyl acetyl succinate as, for example, described in U.S. Pat. No. 5,189,215. Diethyl acetyl succinate can be made from diethyl maleate, which in general is derived from petrochemical based maleic acid anhydride.

Another process for the production of levulinic acid is a process that produces levulinic acid from furfuryl alcohol or its esters. An example of such a process is described in U.S. Pat. No. 4,236,021. Furfurylalcohol is converted at 125° C. to butyl levulinate in the presence of an alcohol, such as butylalcohol, with HCl as catalyst. Butyl levulinate is isolated via distillation. After hydrolysis in an aqueous environment levulinic acid is obtained.

A third process for the production of levulinic acid is by acid catalyzed hydrolysis of C6 carbohydrate-containing feedstocks. The production of levulinic acid by acid catalyzed hydrolysis of C6 carbohydrate-containing feedstocks is described e.g. in WO2010/030617, US2010/312006, U.S. Pat. Nos. 5,608,105, 4,897,497 and 6,054,611.

WO 2014/087013 describes a process to isolate levulinic acid from compositions made by acid hydrolysis of lignocellulosic biomass. However, the levulinic acid compositions produced contain large quantities of angelica lactone which can be detrimental. Additionally, there is no formic acid in the final product.

For the purpose of the present invention levulinic acid is produced by acid catalyzed hydrolysis of a C6 carbohydrate-containing feedstock.

SUMMARY OF THE INVENTION

The processes described in the present application to produce the levulinic acid compositions are novel, useful and different from those typically applied in the processes according to the prior art. The purification of the reaction product X that is directly obtained after acid hydrolyses of C6 carbohydrate-containing feedstock is performed markedly different from the prior art. Therefore, the final levulinic acid composition will differ in the concentration and type of by-products.

One example of a contaminant in the levulinic acid is formic acid.

It was surprisingly discovered that small amounts of formic acid in a levulinic acid composition is not detrimental for the use of levulinic acid in many applications and will even improve the performance of levulinic acid in some applications.

An example is the application of levulinic acid or its ester in the hydrogenation to gamma valerolactone, and/or 1,4-pentanediol, and/or methyltetrathydrofuran (MeTHF). Surprisingly, it was discovered that small amounts of formic acid in the levulinic acid alters the ratio of MeTHF/1,4-pentanediol in favor of MeTHF. The ratio of MeTHF/1,4-pentanediol can be tuned via variation of the formic acid concentration in the levulinic acid.

DETAILED DESCRIPTION OF THE INVENTION

The invention is directed to a levulinic acid composition A comprising: a. at least 95 wt. % of levulinic acid; and b. between 5 wppm and 5000 wppm of formic acid, based on the total weight of the composition, and c. less than 1000 wppm of angelica lactone, based on the total weight of the composition.

An advantage of the composition according to the invention is the improved color stability. Amounts of angelica lactone above 1000 wppm can form colored compounds in the levulinc acid composition.

The amount of levulinic acid in composition A is at least 95 wt. % based on the total weight of the composition. Preferably, the amount of levulinic acid is at least 98 wt. %, more preferably at least 99 wt. %.

The amount of formic acid in composition A is an amount between 5 and 5000 wppm based on the total weight of the composition. Preferably, the amount of formic acid is between 10 and 1000 wppm, more preferably between 20 and 500 wppm.

The amount of angelica lactone in the composition is less than 1000 wppm based on the total weight of the composition. Preferably, the amount of angelica lactone is less than 100 wppm, more preferably less than 10 wppm. Angelica lactone is a cyclic dehydration product of levulinic acid. It is also called 4-hydroxy-3-pentenoic acid γ-lactone or 5-methyl-2(3H)-furanone.

Here and hereafter wppm is the abbreviation of 'weight parts per million'.

When, the amounts of levulinic acid, formic acid and angelica lactone in the composition are less than 98.6 wt. %, based on the total weight of the composition, the balance of the composition is solvent.

The solvent in composition A can be water, an organic solvent or mixtures thereof. Examples of organic solvents are acetic acid and propionic acid; alcohols, such as methanol and ethanol; methyltetrahydrofuran (MTHF), methyl isoamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, methylene chloride, methyl isobutyl carbinol, anisol, ethylene glycol di-n-butyl ether, diethyl carbonate, methyl salicylate, methyl levulinate, ethyl levulinate, toluene, methyl-tertiary butyl ether, hexane, cyclohexane, chloro-benzene, dichloroethane, ortho-dichlorobenzene, 2,6-dimethyl cyclohexanone, tetrahydrofuran, furfural and mixtures thereof.

The composition A according to the invention can comprise other by-products.

These by-products are formed during the acid catalyzed hydrolysis of a C6 carbohydrate-containing feedstock and comprise monomers, dimers, oligomers and polymers. This is a complex reaction mixture wherefrom levulinic acid has to be recovered and purified. These by-products are here and hereafter also called impurities. The by-products can form char in the reaction solution. Char comprises insoluble compounds which can be removed via traditional solid liquid separation steps such as decanting, filtering and other solid liquid separation technologies.

Examples of other by-products are compounds with a boiling point higher than the boiling point of levulinic acid or compounds with a boiling point lower than the boiling point of levulinic acid.

Examples of compounds with a boiling point higher than the boiling point of levulinic acid are, for example, remains of char and tar in solution 1.

Tar is a term summarizing soluble compounds derived from the reaction of C6 carbohydrate-containing feedstock to levulinic acid or derivatives of the C6 carbohydrate-containing feedstock being soluble or partly soluble in solution X. In particular it is known that tar, in the literature also called soluble humins, are derived from the reaction of intermediates of the levulinic acid reaction such as glucose or 5-hydroxymethylfurfural (https://www.rug.nl/research/portal/files/2847282/2006ChemEngResDesGrisuta.pdf, page 5 left column). More specifically it is suggested that the aldol addition and condensation of 2,5-dioxo-6-hydroxyhexanal, an intermediate produced from 5-hydroxymethylfurfural, with aldehydes and ketones that are available in the reacting solution is a predominant pathway for humin formation. It has been shown that when 5-hydrolymethylfurfural is used as the reactant, its furan ring is incorporated into the humins. (http://www3.aiche.org/proceedings/Abstractaspx?PaperID=325434) Additionally, degradation products of the C6 carbohydrate-containing feedstock such as soluble lignin fragments, proteins, fats and uronic acid can be present in tar.

The amount of these by-products in composition A is at most 4.5 wt. %, preferably at most 2 wt. %, more preferably at most 1 wt. %, based on the total weight of the composition.

Formic acid is a by-product during the production of levulinic acid by acid catalyzed hydrolysis of a C6 carbohydrate-containing feedstock. During purification of a reaction product X, that is obtained during acid catalyzed hydrolysis, most of the formic acid is removed from the levulinic acid. However, a small amount, between 5 and 5000 wppm, remains present in the levulinic acid when the levulinic acid is purified according to the purification process as described below. For some applications of the levulinic acid it is advantageous that formic acid is present in the levulinic acid. When the amount of formic acid in the levulinic acid is too low after purification, formic acid can be added from an external source. Preferably, at least 90 wt. % of the formic acid that is present in the composition is not added from an external source.

The invention is further directed to a process for the isolation of a levulinic acid composition comprising the following steps: a. Performing acid catalyzed hydrolysis of a C6 carbohydrate-containing feedstock to obtain reaction product X, b. Subjecting of reaction product X by solid-liquid separation to provide a composition 1, c. Feeding composition 1 to at least two purification steps to treat composition 1 to obtain a levulinic acid composition, wherein a second or a further purification step is a melt crystallization step.

The process according to the invention starts with acid catalyzed hydrolysis of a C6 carbohydrate-containing feedstock to obtain reaction product X.

A C6-carbohydrate is herewith defined as a compound consisting of carbon (C), hydrogen (H) and oxygen (O) atoms. In its monomeric form it usually comprises 6 carbon atoms and has a hydrogen atom:oxygen atom ratio of 2:1.

A C6-carbohydrate-containing feedstock is for example a feedstock comprising monosaccharides, such as fructose, mannose and glucose; disaccharides such as saccharose and lactose and polysaccharides such as starch and cellulose. A C6-carbohydrate-containing feedstock can also be a lignocellulosic feedstock, which comprises cellulose, hemicellulose and lignin.

Examples of lignocellulosic feedstock are wood; wood processing side products such as saw dust, wood chippings and wood shavings; grass; cereals; algae; tree bark; hay; straw; leaves and paper pulp. For the purpose of this application a C6 carbohydrate-containing feedstock comprises at least 20 wt. % C6 carbohydrates.

The feedstock is treated by acid catalyzed hydrolysis. Various acid catalysts are suitable for use during acid catalyzed hydrolysis. These include, but are not limited to, inorganic acids such as sulfuric acid, fluorosulfonic acid, hydrochloric acid, nitric acid, phosphoric acid, benzenesulfonic acid, phosphotungstic acid, phosphomolybdic acid; organic acids such as p-toluene sulfonic acid, trifluoromethanesulfonic acid, 1,1,2,2-tetrafluoroethanesulfonic acid, 1,1,2,3,3,3-hexapropanesulfonic acid, and mixtures thereof; acidic-ion exchange resins; Brönsted acid catalysts such as bismuth triflate, yttrium triflate, ytterbium triflate, neodymium triflate, lanthanum triflate, scandium triflate, zirconium triflate, and $Zn(BF_4)_2$; fluorinated sulfonic acid polymers; metal salts of acid such as metal sulfonates, metal sulfates, metal trifluoroacetates, metal triflates; heteropolyacids; and perfluoroalkylsulfonic acids.

By performing acid catalyzed hydrolysis of a C6 carbohydrate-containing feedstock a reaction product X is obtained. Reaction product X comprises levulinic acid, formic acid and other by-products. Reaction product X needs to be purified to isolate and concentrate the levulinic acid and to obtain a levulinic acid composition.

After performing the acid catalyzed hydrolysis of the C6 carbohydrate-containing feedstock the reaction product X is purified. Reaction product X can be neutralized by a base before further treatment takes place. Bases can be, for example, inorganic base such as sodium hydroxide, sodium carbonate, calcium hydroxide, calcium carbonate, liquid gaseous or dissolved ammonia.

Thereafter, a solid-liquid separation takes place according to step b. Examples of solid-liquid separation are filtration and centrifugation. Solid-liquid separation can be performed after the reactor to remove the solid char and/or salts from the reaction product X. After solid-liquid separation composition 1 is obtained.

Composition 1 is purified by feeding composition 1 to at least two purification steps to treat composition 1 and to obtain a levulinic acid composition.

The process preferably comprises 2-8 purification steps, more preferably 2-6 purification steps, most preferably 2-4 purification steps.

Composition 1 is treated in at least two purification steps. Examples of purification steps are distillation steps, extraction steps, evaporation steps and crystallization steps.

Preferably, a first purification step according to step c is chosen from a distillation step, an extraction step and/or an evaporation step.

According to the prior art a composition 1 is often only purified by distillation. By using only distillation steps for the purification the required purity of a levulinic acid composition will not be obtained. Moreover applying distillation in the purification of levulinic acid will yield a product with high concentrations of angelica lactone. (see WO 2014/087017). High concentrations of angelica lactone have to be removed or treated in separate unit operations to arrive at a levulinic acid with the desired quality. High concentrations of angelica lactone will also reduce the color stability of the levulinic acid composition.

Distillation is a process of separating the components from a liquid reaction mixture by selective evaporation and condensation. In industrial processes fractional distillation is commonly used in order to separate the components by repeated vaporization-condensation cycles within a fractionating column. A process comprising successive distillations, is also referred to as rectification.

Extraction is a process that uses two immiscible phases to separate a solute from one phase into the other. The most commonly used extraction process is liquid-liquid extraction, wherein two immiscible liquids are used to cause separation of components in a mixture.

Preferably, the first purification step of step c in the process according to the invention is an evaporation step.

An evaporator is a device that is used to turn the liquid form of a chemical or solvent into its vapor form. By heat the liquid in the solution is vaporized. The vapor or part of the vapor is removed from the remaining solution and is condensed. Heating the solutions comprising levulinic acid can be performed at atmospheric pressure or at reduced pressure. Preferably, the solutions comprising levulinic acid are treated at reduced pressure.

By treating solutions comprising levulinic acid solvent and/or impurities can be removed from the solutions.

The process of evaporation is widely used to concentrate solutions of chemicals. In the concentration process, the aim of evaporation in step b is to vaporize most of the water and/or other solvents from a solution which contains the desired product. In the chemical industry, the evaporation process is used to eliminate excess moisture, providing a product and improving product stability. Heat is added to the solution, and part of the solvent is converted into vapor. Heat is the main driving force in evaporation, and the evaporation process occurs more readily at higher temperature and lower pressure. Heat is needed to provide enough energy for the molecules of the solvent to leave the solution and move into the vapor phase. Heat can be provided by various sources that can be in direct or indirect contact with the solution containing the desired product. Examples for heating sources that are in indirect contact with the solution are heating coils or a heating mantle. In the heating coils or heating mantle a heating medium is present that provides the heat. The heating medium can also be in direct contact with the solution. Examples of heating media are steam or any other hot liquid or gaseous stream.

Evaporators can be classified into four different categories:
Evaporators in which a heating medium is not in direct contact with the evaporating liquid by tubular heating surfaces.
Evaporators in which a heating medium is confined by coils, jackets, double walls etc.
Evaporators in which a heating medium is brought into direct contact with the evaporating fluid.
Evaporators in which heating is done with solar radiation.

The process of evaporation is widely used to concentrate solutions of chemicals. In the concentration process, the aim of evaporation in step b is to vaporize most of the water and/or other solvents from a solution which contains the desired product. In the chemical industry, the evaporation process is used to eliminate excess moisture, providing a product and improving product stability. Heat is added to the solution, and part of the solvent is converted into vapor. Heat is the main driving force in evaporation, and the evaporation process occurs more readily at higher temperature and lower pressure. Heat is needed to provide enough energy for the molecules of the solvent to leave the solution and move into the vapor phase. Heat can be provided by various sources, for example heating coils or a heating mantle, steam or any other hot liquid or gaseous stream. In the evaporator the steam can be in direct or indirect contact with the solution containing the desired product.

The evaporator or evaporators in the evaporation step can be chosen from the group of kettle evaporators, internal reboilers, thermo-syphon evaporators, plate and frame heat exchangers, spiral wound heat exchangers, shell and tube heat exchangers, forced circulation evaporators, falling film evaporators, rising film evaporators or agitated thin film evaporators.

Preferably, the evaporator or evaporators is/are operated at a liquid temperature between 100 and 200° C. The liquid temperature is preferably higher than 110° C., more preferably higher than 120° C. The liquid temperature is preferably lower than 190° C., more preferably lower than 180° C.

A second or a further purification step in step c of the isolation process is a melt crystallization step.

Melt crystallization can be performed in different ways. Melt crystallization is well described in the literature for example in Jansens P. J. and Matsuoka M.: "Melt Crystallization", in: Encyclopedia of Separation Science, Eds. Wilson I. D., Adlard E. R., Cook M., and Poole C. F., Academic Press, San Diego, New York London, Sidney, Tokyo, (2000) 966-975 and in Arkenbout G. F., Melt crystallization technology", Technomic Publishing Company, Inc., Lancaster, Pa. USA, (1995) 239-290.

An example of a melt crystallization process is layered growth melt crystallization. During layered growth melt crystallization the crystals grow as a layer on a cooled surface. The growth of the crystals is perpendicular to the surface. Industrial equipment for layer growth melt crystallization is normally operated batch-wise, whereby static and dynamic processes can be distinguished. In static processes the crystal growth occurs from a stagnant melt.

A melt crystallization cycle can comprise the following steps:
i. Feeding composition 1 to a melt crystallizer, wherein composition 1 is cooled to the freezing point or below the freezing point of levulinic acid to crystallize the levulinic acid in composition 1,
ii. Separating a liquid 1 from the crystallized levulinic acid,
iii. Melting the crystals obtained according to step a, after separation of liquid 1, to obtain a composition 2.

An example of such a process is suspension melt crystallization. During suspension melt crystallization the crystals form and grow while the crystals are suspended in composition 1. After crystal growth the crystals can be separated according to step b by filtering or any other solid liquid separation technology.

A melt crystallization cycle can also comprise two additional steps between step ii and step iii. According to these additional steps the crystals obtained in step i are treated at raised temperature after draining of liquid 1. By this treatment the crystals are partly melted and a liquid 2 is obtained. This treatment is also called sweating. In a following step the liquid 2 is drained from the crystals.

In dynamic crystallization processes there is forced mixing of composition 1 during cooling in step i. Mixing is usually achieved by the circulation of composition 1 as a falling film or a flow over vertical heat-exchanger tubes, but other designs are also possible. Preferably, the melt crystallizer is a static crystallizer, more preferably at least one of the crystallizers that are used in the process according to the invention is a static crystallizer.

In a preferred embodiment of the invention, the purification step comprises 1-3 evaporation steps in series followed by at least one melt crystallization step.

The invention is further directed to the use of a levulinic acid composition as a feedstock for a process for the production of methyltetrathydrofuran (MeTHF).

Levulinic acid or its ester can be used in a hydrogenation reaction for the production of gamma valerolactone, and/or 1,4-pentanediol, and/or methyltetrahydrofuran (MeTHF). Surprisingly, it was discovered that small amounts of formic acid in the levulinic acid alters the ratio of MeTHF/1,4-pentanediol in favor of MeTHF. The ratio of MeTHF/1,4-pentanediol can be tuned via variation of the formic acid concentration in the levulinic acid.

Example

A pretreatment reactor was conditioned by adding 5 tons of water. Thereafter, water was fed with a flow of 2500 kg/h at a temperature of about 90° C. and the other ingredients were fed as well. Dry corn with a flow of 500 kg/h and HCl 32% (Chimpex Industriale) with a flow of 250 kg/h. Everything was homogeneously mixed in the pretreatment reactor. The slurry contained about 2.6 wt. % HCl and 15 wt. % corn and the total flow was 3250 kg/h. The mixture was pumped to the reactor and heated with 1300 kg/h steam of 17 bar (210° C.) up to 12 bar (185° C.). The total flow became 4550 kg/h. The residence time in the reactor was 1 hour. The stream leaving the reactor contained levulinic acid (LA) 150 kg/h, formic acid (FA) 50 kg/h, solid char 120 kg/h, tar 140 kg/h and intermediate boiling solubles 10 kg/h. Intermediate boiling solubles are compounds with a boiling point between the boiling point of levulinic acid and the boiling point of formic acid. The solution leaving the reactor was flashed in a flash tank to atmospheric pressure hereby venting the steam (1300 kg/h) that was needed to heat the reactor. The slurry was partially neutralized (to a pH of 3) with 300 kg/h soda 30% (Chimpex Industriale, 90 kg/h soda absolute) and the total flow became 3550 kg/h. During the neutralization water was made as well as salt (130 kg/h). The slurry was filtered and char was separated with a moisture content of about 42 wt. %. The total char removal was about 210 kg/h. Therefore the final flow was 3340 kg/h. The process was continued for 5.8 hours until a total amount of slurry of 19372 kg was made. Together with the 5 initial tons of water this made about 24400 kg that contained 850 kg of LA (3.4 wt. %), 260 of FA (1.1 wt. %), 740 kg (3 wt. %) of salt and 850 kg (3.4 wt. %) of tar and intermediate soluble boilers.

A part of total slurry (10.7 tons) was concentrated in a horizontal evaporator heated by thermal oil in a heat exchanger. The temperature of the thermal oil in the evaporator gradually increased from 140° C. until 180° C. was reached. In the same period the pressure was reduced from 1 bar to 500 mbar. In the final portion of the evaporator the salts precipitated and were removed and the final solution had a total mass of 3.6 ton containing 360 kg LA (10 wt. %), 108 kg FA (3 wt. %), 360 kg tar and intermediate boilers (10 wt. %) and 180 kg salts (5 wt. %).

From this solution levulinic acid was recovered via a series of thin film evaporators.

In a first Forced Circulated Evaporator the major amount of water was removed. The evaporator was operated with a liquid temperature of 150° C. and a pressure of 150 mbar. 125 kg/h of the final solution mentioned above was split in a top stream (91.95 kg/h) and a bottom stream (33.05 kg/h) in the evaporator. The top stream contained 0.125 kg/h LA (0.14 wt. %), 3.48 kg/h FA (3.8 wt. %), and 88.35 kg/h water (96.1 wt. %). The bottom stream had 12.38 kg/h LA (37.4 wt. %), 0.28 kg/h FA (0.8 wt. %), 1.65 kg/h water (5 wt. %), 6.25 kg/h salts (18.9 wt. %) and 12.5 kg/g tar and intermediate boilers (37.8 wt. %).

The lights of this bottom stream were removed in a first agitated thin film evaporator. The evaporator was operated with a bottom temperature of 150° C. and at a pressure of 30 mbar. The top stream contained 9 wt. % LA (0.17 kg/h), 8 wt. % FA (0.15 kg/h), 75 wt. % water (1.41 kg/h) and 8 wt. % intermediate boilers (0.15 kg/h). The total mass flow was 1.88 kg/h. The bottom stream had a size of 31.17 kg/h and contained 39.2 wt. % LA (12.2 kg/h), 0.4 wt. % FA (0.125 kg/h), 0.8 wt. % water (0.24 kg/h) and 39.6 wt. % tar and intermediate boilers (12.34 kg/h) and 18.9 wt. % salts (6.25 kg/h).

The levulinic acid in the viscous bottom stream was recovered in a second agitated thin film evaporator. The evaporator was operated with a liquid temperature of 150° C. and at a pressure of 10 mbar. The top stream contained 90.7 wt. % LA (11.66 kg/h), 0.4 wt. % FA (0.05 kg/h), 1.9 wt. % water (0.24 kg/h) and 7 wt. % intermediate boilers (12.35 kg/h). The total mass flow was 12.85 kg/h. The bottom stream had a size of 18.32 kg/h and contained 3 wt. % LA (0.55 kg/h), 0.4 wt. % FA (0.07 kg/h), 62.5 wt. % heavy boilers (11.45 kg/h) and 18.9 wt. % salts (6.25 kg/h). An angelica lactone concentration above 1000 wppm was not detected. That gave a recovery of levulinic acid over the series of film evaporators of 93.2 wt. %.

1000 grams of the 90.7 wt. % of a levulinic acid (LA) solution was fed to a laboratory scale static melt crystallizer. The static melt crystallizer was a jacketed glass vessel (volume 5 l.) equipped with a stainless steel U-tube for cooling. The U-tube was submerged in the feed solution.

The first crystallization step was carried out at 10° C. for 6 hours. The temperature was determined in the levulinic acid solution. After the crystal growth phase, the liquid 1 of crystallization step 1 was drained from the crystals. The crystals, attached to the wall of the U-tube, were subjected to a sweating phase in order to remove the impurities. The sweating phase lasted for 3 hours at a temperature of 20° C. and the sweating liquid 2 of crystallization step 1 was drained. The temperature of 20° C. was the temperature of the cooling medium.

After the sweating phase, the crystals were melted by bringing the temperature of the cooling medium in the U-tube to 40° C. The crystals melted from the U-tube surface. 358 grams of melted levulinic acid crystals were obtained with a purity of 96.1 wt. % LA and 2.7 wt. % of water. Formic acid was present in a concentration between 5 wppm and 5000 wppm, angelica lactone present in a concentration below 1000 wppm. The concentration of intermediate boilers closed the mass balance to 100%.

The 358 grams melt from the first crystallization step was subjected to a second crystallization step, carried out at 15° C., also for 6 hours. The crystallization temperature was determined in the levulinic acid product. After draining the liquid 2 of crystallization 2 the crystals were subjected to sweating at 30° C. for a period of 3 hours and the sweating liquid 2.2 was drained. The temperature during sweating was the temperature of the cooling medium. The crystals were melted to yield 104 grams of melted crystals with a purity of 99%, Moreover the melt was colorless. The concentration of water was below 0.9 wt. %, the concentration of angelica lactone was below 1000 wppm and the concentration of formic acid was below 400 wppm. The concentration of intermediate boilers closed the mass balance to 100%.

What is claimed is:

1. A levulinic acid composition A, comprising:
at least 98 wt. % of levulinic acid;
between 5 wppm and 5000 wppm of formic acid; and
less than 1000 wppm of angelica lactone, based on the total weight of the composition, and
when the amounts of levulinic acid, formic acid and angelica lactone in the composition are less than 98.6 wt. %, based on the total weight of the composition, the balance of the composition is solvent; and
wherein the levulinic acid composition A is obtained by purification through melt crystallization.

2. The composition according to claim 1, wherein the amount of levulinic acid is at least 99 wt. %, based on the total weight of the composition.

3. The composition according to claim 1, wherein the amount of formic acid is between 10 wppm and 1000 wppm, based on the total weight of the composition.

4. The composition according to claim 1, wherein the amount of formic acid is between 20 wppm and 500 wppm, based on the total weight of the composition.

5. The composition according to claim 1, wherein the amount of angelica lactone is 100 wppm.

6. The composition according to claim 1, wherein the amount of angelica lactone is 10 wppm.

7. The composition according to claim 1, wherein at least 90 wt. % of the formic acid that is present in the composition was not added from an external source.

8. A process for the isolation of the levulinic acid composition of claim 1, comprising the following steps:
performing acid catalyzed hydrolysis of a C6 carbohydrate-containing feedstock to obtain reaction product X,
subjecting of reaction product X to solid-liquid separation to provide a composition 1,
feeding composition 1 to at least two purification steps to treat composition 1 to obtain a levulinic acid composition, wherein a second or a further purification step is a melt crystallization step.

9. The process according to claim 8, wherein the process comprises 2-8 purification steps.

10. The process according to claim 8, wherein a first purification step is chosen from a distillation step, an extraction step and/or an evaporation step.

11. The process according to claim 8, wherein a first purification step is an evaporation step.

12. The process according to claim 8, wherein the purification step comprises 1-3 evaporation steps in series followed by at least one melt crystallization step.

13. Use of a levulinic acid composition according to claim 1, as a feedstock for a process for the production of methyltetrathydrofuran (MeTHF).

14. The composition according to claim 2, wherein the amount of formic acid is between 10 wppm and 1000 wppm, based on the total weight of the composition, and wherein the amount of formic acid is between 20 wppm and 500 wppm, based on the total weight of the composition.

15. The composition according to claim 14, wherein the amount of angelica lactone is 100 wppm, and wherein at least 90 wt. % of the formic acid that is present in the composition was not added from an external source.

16. The process according to claim 10, wherein a first purification step is an evaporation step.

17. The process according to claim 16, wherein the purification step comprises 1-3 evaporation steps in series followed by at least one melt crystallization step.

* * * * *